United States Patent
Chomas et al.

(10) Patent No.: US 9,089,341 B2
(45) Date of Patent: Jul. 28, 2015

(54) RENAL NERVE NEUROMODULATION DEVICE

(75) Inventors: James E. Chomas, Denver, CO (US); Norman R. Weldon, Evergreen, CO (US); Leonard Pinchuk, Miami, FL (US)

(73) Assignee: SUREFIRE MEDICAL, INC., Westminster, CO (US)

(*) Notice: Subject to any disclaimer, the term of this patent is extended or adjusted under 35 U.S.C. 154(b) by 767 days.

(21) Appl. No.: 13/407,088

(22) Filed: Feb. 28, 2012

(65) Prior Publication Data
US 2013/0226166 A1  Aug. 29, 2013

(51) Int. Cl.
*A61B 18/14* (2006.01)
*A61B 18/00* (2006.01)

(52) U.S. Cl.
CPC ... *A61B 18/1492* (2013.01); *A61B 2018/00214* (2013.01); *A61B 2018/00267* (2013.01); *A61B 2018/00404* (2013.01); *A61B 2018/00434* (2013.01); *A61B 2018/00511* (2013.01); *A61B 2018/00577* (2013.01); *A61B 2018/00839* (2013.01)

(58) Field of Classification Search
CPC ........ A61B 18/1492; A61B 2018/00577; A61B 18/00214; A61B 18/00642; A61B 18/00744; A61B 2019/464; A61B 8/12; A61B 5/0084; A61B 2018/00434; A61B 5/03; A61B 5/6876
See application file for complete search history.

(56) References Cited

U.S. PATENT DOCUMENTS

| | | | |
|---|---|---|---|
| 4,738,740 A | 4/1988 | Pinchuk et al. | |
| 5,234,425 A | 8/1993 | Fogarty et al. | |
| 5,893,869 A | 4/1999 | Barnhart et al. | |
| 5,895,399 A | 4/1999 | Barbut et al. | |
| 5,910,154 A | 6/1999 | Tsugita et al. | |
| 5,911,734 A | 6/1999 | Tsugita et al. | |
| 6,001,118 A | 12/1999 | Daniel et al. | |
| 6,010,522 A | 1/2000 | Barbut et al. | |
| 6,027,520 A | 2/2000 | Tsugita et al. | |

(Continued)

FOREIGN PATENT DOCUMENTS

| | | |
|---|---|---|
| EP | 1226795 | 7/2002 |
| EP | 1803423 | 7/2007 |

(Continued)

OTHER PUBLICATIONS

Fusion Drug Delivery System-Novel Catheter/Stent Design for Targeted Drug Delivery, Gerschwind & Barnett, Non-Published US provisional patent application filed Sep. 17, 2007.

(Continued)

*Primary Examiner* — Deborah Malamud
(74) *Attorney, Agent, or Firm* — Gordon & Jacobson, PC

(57) ABSTRACT

A neuromodulation device includes an ablation valve with electrodes provided about its circumference. The valve dynamically reacts to fluid pressure within the vessel. When a pressure within and distal said ablation valve is greater than the body fluid pressure within the vessel, said ablation valve closes and the electrodes move out of contact with the endothelium of the vessel. When a pressure within and distal the ablation valve is less than the body fluid pressure upstream of the valve, the valve opens such that the electrodes are in circumferential contact with the endothelium. Fluid can be injected into the valve to alter the local pressure about the valve and force the electrodes into contact with the endothelium.

17 Claims, 8 Drawing Sheets

(56) References Cited

U.S. PATENT DOCUMENTS

| | | |
|---|---|---|
| 6,042,598 A | 3/2000 | Tsugita et al. |
| 6,059,745 A | 5/2000 | Gelbfish |
| 6,152,946 A | 11/2000 | Broome et al. |
| 6,165,200 A | 12/2000 | Tsugita et al. |
| 6,168,579 B1 | 1/2001 | Tsugita |
| 6,179,851 B1 | 1/2001 | Barbut et al. |
| 6,235,044 B1 | 5/2001 | Root et al. |
| 6,258,120 B1 | 7/2001 | McKenzie et al. |
| 6,306,074 B1 | 10/2001 | Waksman et al. |
| 6,306,163 B1 | 10/2001 | Fitz |
| 6,309,399 B1 | 10/2001 | Barbut et al. |
| 6,361,545 B1 | 3/2002 | Macoviak et al. |
| 6,371,969 B1 | 4/2002 | Tsugita et al. |
| 6,371,971 B1 | 4/2002 | Tsugita et al. |
| 6,383,206 B1 | 5/2002 | Gillick et al. |
| 6,395,014 B1 | 5/2002 | Macoviak et al. |
| 6,436,112 B2 | 8/2002 | Wensel et al. |
| 6,443,926 B1 | 9/2002 | Kletschka |
| 6,485,456 B1 | 11/2002 | Kletschka |
| 6,485,502 B2 | 11/2002 | Don Michael et al. |
| 6,499,487 B1 | 12/2002 | McKenzie et al. |
| 6,530,935 B2 | 3/2003 | Wensel et al. |
| 6,533,800 B1 | 3/2003 | Barbut |
| 6,537,294 B1 | 3/2003 | Boyle et al. |
| 6,537,297 B2 | 3/2003 | Tsugita et al. |
| 6,540,722 B1 | 4/2003 | Boyle et al. |
| 6,551,303 B1 | 4/2003 | Van Tassel et al. |
| 6,582,396 B1 | 6/2003 | Parodi |
| 6,589,264 B1 | 7/2003 | Barbut et al. |
| 6,592,546 B1 | 7/2003 | Barbut et al. |
| 6,607,506 B2 | 8/2003 | Kletschka |
| 6,620,148 B1 | 9/2003 | Tsugita |
| 6,635,070 B2 | 10/2003 | Leeflang et al. |
| 6,645,220 B1 | 11/2003 | Huter et al. |
| 6,645,222 B1 | 11/2003 | Parodi et al. |
| 6,645,223 B2 | 11/2003 | Boyle et al. |
| 6,652,555 B1 | 11/2003 | VanTassel et al. |
| 6,652,556 B1 | 11/2003 | VanTassel et al. |
| 6,656,351 B2 | 12/2003 | Boyle |
| 6,673,090 B2 | 1/2004 | Root et al. |
| 6,676,682 B1 | 1/2004 | Tsugita et al. |
| 6,689,150 B1 | 2/2004 | VanTassel et al. |
| 6,692,508 B2 | 2/2004 | Wensel et al. |
| 6,692,509 B2 | 2/2004 | Wensel et al. |
| 6,692,513 B2 | 2/2004 | Streeter et al. |
| 6,695,813 B1 | 2/2004 | Boyle et al. |
| 6,695,858 B1 | 2/2004 | Dubrul et al. |
| 6,702,834 B1 | 3/2004 | Boylan et al. |
| 6,706,053 B1 | 3/2004 | Boylan et al. |
| 6,706,055 B2 | 3/2004 | Douk et al. |
| 6,730,108 B2 | 5/2004 | VanTassel et al. |
| 6,746,469 B2 | 6/2004 | Mouw |
| 6,818,006 B2 | 11/2004 | Douk et al. |
| 6,830,579 B2 | 12/2004 | Barbut |
| 6,837,898 B2 | 1/2005 | Boyle et al. |
| 6,855,154 B2 | 2/2005 | Abdel-Gawwad |
| 6,866,677 B2 | 3/2005 | Douk et al. |
| 6,887,258 B2 | 5/2005 | Denison et al. |
| 6,896,690 B1 | 5/2005 | Lambrecht et al. |
| 6,902,540 B2 | 6/2005 | Dorros et al. |
| 6,908,474 B2 | 6/2005 | Hogendijk et al. |
| 6,911,036 B2 | 6/2005 | Douk et al. |
| 6,936,060 B2 | 8/2005 | Hogendijk et al. |
| 6,939,362 B2 | 9/2005 | Boyle et al. |
| 6,964,670 B1 | 11/2005 | Shah et al. |
| 6,964,673 B2 | 11/2005 | Tsugita et al. |
| 6,974,469 B2 | 12/2005 | Broome et al. |
| 6,989,027 B2 | 1/2006 | Allen et al. |
| 7,044,958 B2 | 5/2006 | Douk et al. |
| 7,044,966 B2 | 5/2006 | Svanidze et al. |
| 7,066,946 B2 | 6/2006 | Douk et al. |
| 7,101,396 B2 | 9/2006 | Artof et al. |
| 7,162,303 B2 | 1/2007 | Levin et al. |
| 7,169,164 B2 | 1/2007 | Borillo et al. |
| 7,172,614 B2 | 2/2007 | Boyle et al. |
| 7,172,621 B2 | 2/2007 | Theron |
| 7,214,237 B2 | 5/2007 | Don Michael et al. |
| 7,217,255 B2 | 5/2007 | Boyle et al. |
| 7,223,253 B2 | 5/2007 | Hogendijk |
| 7,232,452 B2 | 6/2007 | Adams et al. |
| 7,232,453 B2 | 6/2007 | Shimon |
| 7,241,304 B2 | 7/2007 | Boyle et al. |
| 7,250,041 B2 | 7/2007 | Chiu et al. |
| 7,252,675 B2 | 8/2007 | Denison et al. |
| 7,279,000 B2 | 10/2007 | Cartier et al. |
| 7,306,575 B2 | 12/2007 | Barbut et al. |
| 7,322,957 B2 | 1/2008 | Kletschka et al. |
| 7,326,226 B2 | 2/2008 | Root et al. |
| 7,331,973 B2 | 2/2008 | Gesswein et al. |
| 7,338,510 B2 | 3/2008 | Boylan et al. |
| 7,344,549 B2 | 3/2008 | Boyle et al. |
| 7,371,249 B2 | 5/2008 | Douk et al. |
| 7,425,215 B2 | 9/2008 | Boyle et al. |
| 7,537,600 B2 | 5/2009 | Eskuri |
| 7,544,202 B2 | 6/2009 | Cartier et al. |
| 7,572,272 B2 | 8/2009 | Denison et al. |
| 7,582,100 B2 | 9/2009 | Johnson et al. |
| 7,585,309 B2 | 9/2009 | Larson |
| 7,591,832 B2 | 9/2009 | Eversull et al. |
| 7,604,650 B2 | 10/2009 | Bergheim |
| 7,647,115 B2 | 1/2010 | Levin et al. |
| 7,653,438 B2 | 1/2010 | Deem et al. |
| 7,833,242 B2 | 11/2010 | Gilson et al. |
| 7,842,084 B2 | 11/2010 | Bicer |
| 7,853,333 B2 | 12/2010 | Demarais |
| 7,873,417 B2 | 1/2011 | Demarais |
| 7,937,143 B2 | 5/2011 | Demarais et al. |
| 8,500,775 B2 | 8/2013 | Chomas et al. |
| 8,696,698 B2 | 4/2014 | Chomas et al. |
| 8,696,699 B2 | 4/2014 | Chomas et al. |
| 2002/0161390 A1 | 10/2002 | Mouw |
| 2002/0161394 A1 | 10/2002 | Macoviak et al. |
| 2003/0187474 A1 | 10/2003 | Keegan et al. |
| 2004/0068288 A1 | 4/2004 | Palmer et al. |
| 2004/0220609 A1 | 11/2004 | Douk et al. |
| 2004/0225354 A1 | 11/2004 | Allen et al. |
| 2005/0010285 A1 | 1/2005 | Lambrecht et al. |
| 2005/0015048 A1 | 1/2005 | Chiu et al. |
| 2005/0015112 A1 | 1/2005 | Cohn et al. |
| 2005/0119688 A1 | 6/2005 | Bergheim |
| 2005/0261759 A1 | 11/2005 | Lambrecht et al. |
| 2006/0173490 A1 | 8/2006 | LaFontaine et al. |
| 2007/0106324 A1 | 5/2007 | Garner et al. |
| 2007/0179590 A1 | 8/2007 | Lu et al. |
| 2008/0033341 A1 | 2/2008 | Grad |
| 2008/0039786 A1 | 2/2008 | Epstein et al. |
| 2009/0018498 A1 | 1/2009 | Chiu et al. |
| 2009/0076409 A1 | 3/2009 | Wu et al. |
| 2011/0137399 A1 | 6/2011 | Chomas et al. |
| 2012/0116351 A1 | 5/2012 | Chomas et al. |
| 2013/0079731 A1 | 3/2013 | Chomas et al. |
| 2013/0226166 A1 | 8/2013 | Chomas et al. |
| 2014/0207178 A1 | 7/2014 | Chomas et al. |

FOREIGN PATENT DOCUMENTS

| | | |
|---|---|---|
| WO | WO 99/16382 | 4/1999 |
| WO | WO 99/44510 A1 | 9/1999 |
| WO | WO 01/41679 | 6/2001 |
| WO | WO 01/45592 A1 | 6/2001 |
| WO | WO 01/49215 A2 | 7/2001 |
| WO | WO 2004/043293 | 5/2004 |

OTHER PUBLICATIONS

A Study of the Geometrical and Mechanical Properties of a Self-Expandig Metallic Stent—Theory and Experiment, Dr. Michael R. Jedwab, Claude O. Clerc, Journal of Applied Biomaterials, vol. 4, Issue 1, pp. 77-85, Spring 1993.

Finite Element Stent Design, M. De Beule, R. Van Impe, P. Verdonck, B. Verhegghe, Computer Methods in Biomechanics and Biomedical Engineering, 2005.

(56) References Cited

OTHER PUBLICATIONS

Catheter-Based Renal Sympathetic Denervation for Resistant Hypertension: a Multicentre Safety and Proof-of Principle Cohort Study, Krum et al, The Lancet, 2009.
Renal Denervation as a Therapeutic Approach for Hypertension: Novel Implications for an Old Concept, Schlaich et al., Hypertension, Journal of the American Heart Association, 2009, 54:1195-1201.
Renal Sympathetic-Nerve Ablation for Uncontrolled Hypertension, Schlaich et al, The New England Journal of Medicine, 2009, pp. 932-934.
U.S. Appl. No. 14/259,293 filed Apr. 23, 2014, Bryan Pinchuk et al.
Embolization II, Scientific Session 11, JVIR, Mar. 27, 2012.
Embolization procedure lowers levels of "hunger hormone," leads to weight loss, EurekAlert Public Release, Mar. 7, 2013.
First-In-Man Study of Left Gastric Artery Embolization for Weight Loss, Nicholas Kipshidze et al., ACC.13, E2056, JACC Mar. 12, 2013, vol. 61, Issue 10.
Left Gastric Embolization Leads to Weight Loss, Bariatriac News, Owen Haskins, Dec. 4, 2013.
US 7,169,126, 01/2007, Zadno-Azizi (withdrawn)

RENAL NERVE NEUROMODULATION DEVICE

BACKGROUND OF THE INVENTION

1. Field of Invention

The present invention relates generally to medical devices, and more particularly to therapeutic intravascular devices for reducing hypertension.

2. State of the Art

Hypertension (HTN) or high blood pressure, sometimes arterial hypertension, is a chronic medical condition in which the blood pressure in the arteries is elevated. This requires the heart to work harder than normal to circulate blood through the blood vessels. Blood pressure involves two measurements, systolic and diastolic, which depend on whether the heart muscle is contracting (systole) or relaxed (diastole) between beats. Normal blood pressure is at or below 120/80 mmHg. High blood pressure is said to be present if it is persistently at or above 140/90 mmHg.

Hypertension is classified as either primary (essential) hypertension or secondary hypertension; about 90-95% of cases are categorized as "primary hypertension" which means high blood pressure with no obvious underlying medical cause. The remaining 5-10% of cases (secondary hypertension) are caused by other conditions that affect the kidneys, arteries, heart or endocrine system.

Persistent hypertension is a major risk factor for stroke, myocardial infarction (heart attacks), heart failure and aneurysms of the arteries (e.g. aortic aneurysm), and is a cause of chronic kidney disease. Even moderate elevation of arterial blood pressure is associated with a shortened life expectancy.

Dietary and lifestyle changes can improve blood pressure control and decrease the risk of associated health complications, although drug treatment is often necessary in patients for whom lifestyle changes prove ineffective or insufficient. Several classes of medications, collectively referred to as antihypertensive drugs, are currently available for treating hypertension. However, some patients have proven resistant to reduced hypertension from treatment with drugs, or otherwise are not suitable candidates for such treatment.

It has been suggested that the neuromodulation of nerve fibers adjacent to renal arteries can substantially reduce systolic and diastolic blood pressure. US Pub. No. 2009/0076409 to Wu et al. describes a method of thermally-induced renal denervation (RDN) in which a device is inserted into the renal arteries, expanded into contact with the vessel wall, and operated to induce thermal damage to the renal nerve. Wu et al. states that treatment may require from seconds, to minutes, to days. Although there is some evidence that the device can achieve desired results, it can cause damage to the renal artery and other non-target tissue, and is subject to widely variable outcomes depending upon operator skill. Wu et al. also teaches that the blood flow through the vessel can be obstructed with a balloon, and the heat removed via injection of a thermal fluid. Obstruction of the renal vessel can damage downstream tissues and organs. As yet another alternative, Wu et al. teaches that the blood flow can be permitted continue through the renal vessel, and a thermal fluid can be injected to supplement heat transfer. However, there is no specific coordination between thermal fluid injection and neuromodulation; this can result in too much thermal fluid being administered or the thermal fluid being administered at a non-optimal time in the treatment.

SUMMARY OF THE INVENTION

A neuromodulation device suitable for renal denervation includes an elongate flexible introducer and an expandable ablation valve. The elongate flexible introducer is preferably a catheter defining a longitudinal lumen. One or more conductors extend along the length of the introducer. The conductors may be encased within the wall of the introducer, may extend within a dedicated lumen or lumens therefor, or may extend outside the introducer.

The ablation valve includes conductive filaments defining electrodes. When the ablation valve is inserted into a vessel, the expandable ablation valve dynamically reacts to intravessel pressure conditions and the change in body fluid flow occurring as a result of dynamic pressure conditions within the vessel. During low pressure conditions such as during diastole, and consequent low or static blood flow conditions, the ablation valve expands to achieve wall apposition. During high pressure conditions such as during systole, and resulting high blood flow conditions, the ablation valve collapses out of contact with the vascular wall. Thus the present invention is a dynamic RF treatment device that can be tuned to open and close automatically by local pressure and flow conditions to modulate treatment.

The ablation valve includes an inner layer defined by electrospun fibers, and an expandable structure comprising a braid of filaments which cross over each other (i.e., are braided) and which have a spring bias to assume a preferred crossing angle relative to each other. The filaments include at least a plurality of electrodes, defined by insulated wires selected to be highly thermally and electrically conductive and preferably also to have good spring characteristics. The insulation is removed from the proximal and distal ends of the filaments. Optionally, one or more of the filaments may be non-conductive filaments, such as to aid in desired spring-characteristics of the expandable structure. The braid of filaments and inner layer are coupled together, with the inner layer extending beyond the exposed distal ends of the filaments. Optionally, an outer layer of electrospun fibers may be provided over the filaments. The proximal end of the braid is radially collapsed and coupled to the distal tip of the elongate introducer.

The distal end of the at least one conductor extending along the elongate introducer is coupled to the electrodes of the ablation valve. In a monopolar embodiment of the invention, a single electrical connection is required between the conductor and the proximal ends of the ablation electrodes, the ablation electrodes are not electrically isolated from each other, and a ground plate is provided in contact with the patient. An RF generator is connected to the conductor from the proximal end of the introducer to deliver RF energy to the electrodes of the ablation valve.

In a bipolar embodiment of the device, two electrically isolated conductors are coupled to the proximal ends of two electrically isolated groups of ablation electrodes, and the ablation electrodes are separated into two electrically isolated groups. An RF generator is connected to the isolated conductors from the proximal end of the introducer to deliver RF energy to the electrodes of the ablation valve.

In either the bipolar or monopolar devices, the device is provided in a first state particularly for introducing the ablation valve to the treatment site. In the first state, the ablation valve is preferably kept in a cylindrical collapsed arrangement. This is preferably carried out by inserting the ablation valve and introducer into a delivery catheter for introduction to the treatment site. In a second state, the ablation valve is free to open due to the spring bias in the filaments. This is preferably performed by retracting the delivery catheter relative to the introducer. In the second state, with the proximal end of the ablation valve attached to the introducer, in the bloodstream, if the blood is not flowing distally past the ablation valve, the applicator assumes a substantially frustoconical shape. The distal end of the ablation valve is intended to make contact with the walls of the vessel in which it is deployed. However, the ablation valve is structured such that it will dynamically react to the pressure within the vessel. When the pressure is greater on the upstream side of the valve than downstream, the ablation valve will retreat from the wall into a closed configuration. When there is no significant difference in pressure between the proximal and distal surfaces of the ablation valve, the ablation valve will open toward the vessel wall, but not necessarily maintain contact with the wall. However, when there is greater pressure within the valve or on the downstream side thereof, the valve will deploy open to the wall.

The ablation valve can be forced against the wall by actively modifying the relative pressures upstream and downstream of the ablation valve. When the introducer is a catheter, any time the pressure in the orifice of the catheter (located at the interior mouth of the ablation valve) increases higher than the pressure in the blood vessel, the ablation valve immediately opens and seals to the blood vessel wall. It is important to note that pressure is communicated throughout the vasculature at the speed of sound in blood (1540 m/s). The pressure at the orifice of the catheter can be increased by way of injection of a thermal fluid therethrough. Further, as the thermal fluid is injected to force the ablation valve against the vessel wall, the thermal fluid also transfers heat from within the vessel to prevent damage to non-target tissue.

Thus, the present invention is a dynamic RF treatment device that can be tuned to open and close automatically by local pressure and flow conditions within a vessel, and particularly the renal arteries, in order to modulate treatment. As a result of the changing local pressure and flow conditions, the device can make pulsatile, simultaneous, multiple, circumferential lesions to the renal nerves, while permitting normal flow when no RF treatment is applied. In addition, the pressure can be temporarily modified via the application of fluid pressure at the orifice of the introducer to maintain the ablation valve in an expanded and vessel contacting configuration for as long as desired.

DETAILED DESCRIPTION OF THE PREFERRED EMBODIMENTS

Figure 1:
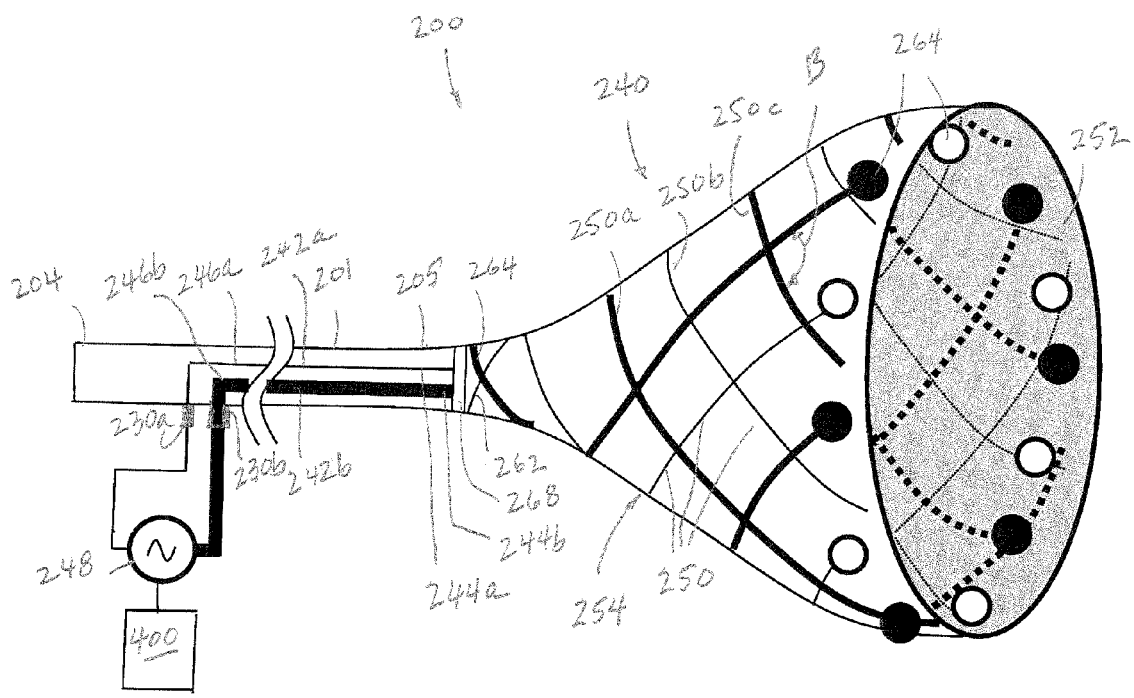
FIG. 1 is a schematic illustration of a first embodiment of a neuromodulation system according to the invention.

Referring to FIG. 1, a neuromodulation device 200 suitable for renal denervation includes an elongate flexible introducer 201 and an expandable ablation valve 240. The elongate flexible introducer 201 is preferably a catheter defining a longitudinal lumen. One or more conductors 242a, 242b extend through or along side the length of the introducer 201. The conductors 242a, 242b may be encased within the wall of the introducer 201, may extend within a dedicated lumen or lumens for the conductors, or may extend outside the introducer. The neuromodulation device may be a bipolar or monopolar device.

In a bipolar device, as shown with reference to FIGS. 1-5A, two conductors 242a, 242b (or two sets of conductors) are electrically insulated from each other. The proximal ends 246a, 246b of the conductors terminate at respective terminals 230a, 230b.

As described in more detail below, the expandable ablation valve 240 includes conductive filaments 250. In the bipolar embodiment, the filaments 250 are arranged in two electrically isolated sets (indicated by white and black). Each set is electrically coupled to the distal end 244a, 244b of one of the conductors 242a, 242b extending along the introducer 201.

An RF sine wave generator 248 is coupled to the terminals 230a, 230b and when powered, the conductive filaments 250 act as neuromodulation electrodes, preferably effective to neuromodulate the renal nerve sufficiently to denervate the renal vessel, such as via ablation.

The ablation valve 240 dynamically reacts to intravascular pressure conditions and the change in blood flow occurring under dynamic pressure conditions within the vessel. During low pressure conditions such as during diastole, and consequent low or static blood flow conditions, the ablation valve expands to achieve wall apposition or near apposition. During high pressure conditions such as systole, and resulting high blood flow conditions, the ablation valve retreats out of contact with the vascular wall. As discussed in detail below, the structure of the ablation valve, by selection of materials and/or construction, can be tuned to open and close automatically by local pressure and flow conditions to modulate treatment. In combination with the application of RF energy from the RF generator 248 to the conductive filaments 250, the device operates as a dynamic RF treatment device.

The device 200 seen in FIG. 1 is not shown to relative size but rather shown for purposes of explanation. An introducer in the form of a catheter 201 has a proximal end 204 and a distal tip 205 defining an orifice. The introducer 201 has sufficient length and longitudinal stiffness to be advanced from outside the body of the patient (not shown) to a target vessel (artery or vein) in the patient, and particularly to the renal artery. The introducer is described in more detail below.

Attached to the distal tip 205 of the introducer 201 is an exemplary embodiment of an ablation valve 240 shown having multiple filaments 250a, 250b, 250c, . . . (or collectively filaments 250) which are preferably braided and can move relative to each other. More particularly, the ablation valve 240 includes an inner insulating fiber layer 252, and a braid layer 254 located over the fiber layer.

The fiber layer 252 is formed by electrospinning fibers on a rotating mandrel (not shown) that is preferably 8 mm±2 mm in diameter. The electrospun fiber layer 252 defines a web of thin filaments, which has a characteristic pore size determined by attempting to pass beads of different diameters therethrough. The very thin filaments can be spun onto a rotating mandrel according to U.S. Pat. No. 4,738,740 with the aid of an electrostatic field or in the absence of an electrostatic field or both. The fiber layer can have some pores formed from electrospinning and then an optional secondary step where pores are laser drilled or formed by a secondary operation. The fiber layer may be made of polyurethane, pellethane, polyolefin, polyester, fluoropolymers, acrylic polymers, acrylates, polycarbonates, or other suitable material. As it is preferred that the polymer be spun onto the mandrel, it is desirable that the polymer be soluble in a solvent. In the preferred embodiment, the fiber layer is formed from polyurethane which is soluble in dimethylacetamide. The polymer material is spun in a liquid state, with a preferred concentration of 5-10% solids for an electrostatic spin process and 15-25% solids for a wet spin process.

Figure 2:
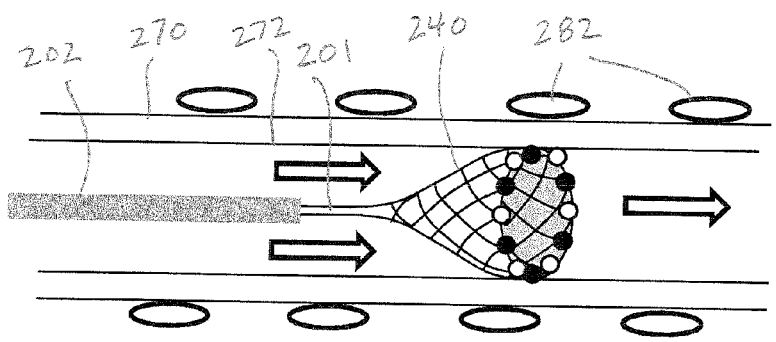
FIG. 2 is a schematic illustration of a distal end portion of the neuromodulation system of FIG. 1 deployed within a renal artery.

The braid layer 254 is initially formed as a tubular form filament braid of preferably 8 to 24 filaments 250, such tubular form dimensioned to be slightly greater in diameter than the mandrel for the fiber layer 252. The filaments 250 have good spring characteristics and are spring biased (i.e., they have "shape memory") to assume a desired crossing angle relative to each other so that the ablation valve can assume a substantially frustoconical shape when the proximal end thereof is radially constrained (it being noted that for purposes herein the term "substantially frustoconical" should be understood to include not only a truncated cone, but a truncated hyperboloid, a truncated paraboloid, and any other shape which starts from a circular proximal end and diverges therefrom). The braid layer 254 comprises at least some wire filaments of a conductive material, such as copper, gold, platinum, or other metal. The conductive wire filaments 250 are also provided with an insulative coating (not shown), such as a polyimide coating, which is stripped from the proximal and distal ends 262, 264 of the filaments. The exposed distal ends 264 of the braid filaments are indicated enlarged relative the remainder of the filaments; this is shown schematically for purposes of highlighting the indicated feature and not as a true representation of the relative size of the exposed ends relative to the remainder of the filaments. The distal ends 264 define the neuromodulation electrode for contacting the endothelium (inner wall) 272 of a vessel 270 (FIG. 2). It is also appreciated that not all of the filaments of the braid need be good conductors and some may be selected for other advantageous properties, such as spring characteristics. Such non-conductive filaments, if provided within the braid layer 254, may be made from, e.g., elastic or superelastic materials including nickel-titanium alloy, spring steels, and non-metallic polymers exhibiting elastic properties. Where polymeric filaments are utilized, the filaments may be composed of polyethylene terephthalate (PET), polyethylene-napthalate (PEN), liquid crystal polymer, fluorinated polymers, nylon, polyamide or any other suitable polymer. The braid layer 254 is preferably composed of shape memory material, either metallic or non-metallic, that is formed and set in a large diameter orientation. One or more of the filaments may be radio-opaque such that it may be tracked in the body. Additionally or alternatively, a radiopaque band or other radiopaque element may be provided to the distal end of the device. The ablation valve is capable of expanding in diameter while reducing in length, and reducing in diameter while expanding in length. The filaments 250 are not bonded to each other along their lengths or, in this embodiment at their distal ends, so to enable the ablation valve 240 to rapidly automatically open and close in response to dynamic flow conditions.

In manufacture, the braid layer 254 is slipped over the insulating fiber layer 252 with the fiber layer preferably extending 2 mm beyond the exposed metal distal end electrodes 264 of the braid filaments. Optionally, an insulating fiber coating of like material to the inner fiber layer 252; i.e., electrospun fibers, is provided over the outside of the braid layer 254. The assembly of the inner fiber and braid layers 252, 254 is then radially collapsed at its proximal end and bonded to the catheter distal tip 205. The exposed proximal metal ends of the conducting filaments 250 of the braid layer 254 are electrically coupled to the distal ends 244a, 244b of the conductors 242a, 242b that extend along the introducer 201. The electrically coupling may be direct connection between the conductors and the conducting filaments or may include an intermediate electrical connection, as shown at collar 268.

It should be appreciated by those skilled in the art that the introducer 201 can be any catheter known in the art. Typically, the catheter will be between two and eight feet long, have an outer diameter of between 0.67 mm and 3 mm (corresponding to catheter sizes 2 French to 9 French), and will be made from a liner made of fluorinated polymer such as polytetrafluoroethylene (PTFE) or fluorinated ethylene propylene (FEP), a braid made of metal such as stainless steel or titanium, or a polymer such as polyethylene terephthalate (PET) or liquid crystal polymer, and an outer coating made of a polyether block amide thermoplastic elastomeric resin such as PEBAX®, polyurethane, polyamide, copolymers of polyamide, polyester, copolymers of polyester, fluorinated polymers, such as PTFE, FEP, polyimides, polycarbonate or any other suitable material, or any other standard or specialty material used in making catheters used in the bloodstream. Furthermore, while it is preferable that the introducer be in the form of a catheter, it is not a requirement of the invention.

As an alternative, the introducer 201 may be in the form of a guidewire or other flexible, yet longitudinally stiff member to which the ablation valve 240 can be attached. However, if the introducer is not a hollow tubular member it will not be possible deliver thermal fluid through the introducer to actively alter the pressure within the ablation valve, as described below.

Referring to FIG. 2, around the introducer 201 is an outer catheter or sleeve 202 which is movable over the introducer 201 and ablation valve 240. If desired, the outer catheter or sleeve 202 can extend the entire length of the introducer. Where the outer catheter or sleeve 202 extends along the entire length of the introducer, it has a proximal end (not shown) which extends proximally and which can be controlled by a practitioner from outside the body of the patient. Alternatively, the outer catheter or sleeve 202 extends only over the distal end of the introducer 201 and ablation valve 240, but is controlled by a control element which extends proximally and which can be controlled by a practitioner from outside the body of the patient.

Sleeve or outer catheter 202 is comprised of a material capable of holding the ablation valve 240 in a cylindrical configuration and capable of sliding over the ablation valve 240 and the catheter 201. Sleeve or outer catheter 202 can be comprised of polyurethane, polyamide, copolymers of polyamide, polyester, copolymers of polyester, fluorinated polymers, such as PTFE, FEP, polyimides, polycarbonate or any other suitable material. The sleeve or outer catheter may also contain a braid composed of metal such as stainless steel or titanium, or a polymer such as PET or liquid crystal polymer, or any other suitable material. The wall thickness of sleeve or outer catheter 202 is preferably in the range of 0.05 mm to 0.25 mm with a more preferred thickness of 0.1 mm-0.15 mm.

Figure 3:
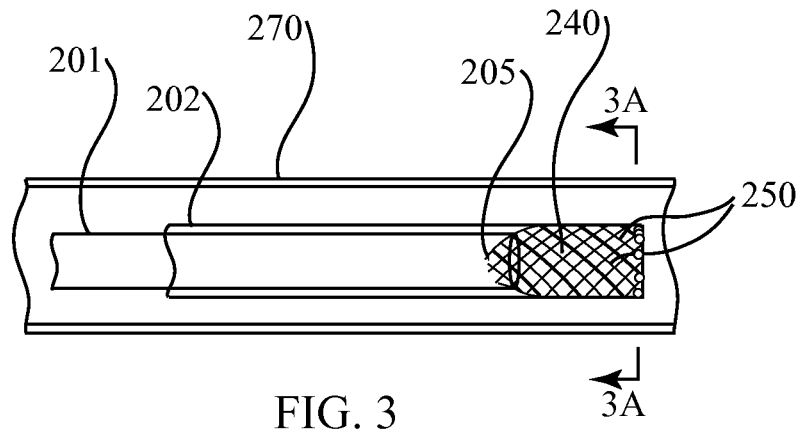
FIG. 3 is a schematic illustration of a distal end portion of the neuromodulation system of FIG. 1 in the renal artery, shown with the ablation valve retracted in an outer sleeve of the device.
Figure 3A:
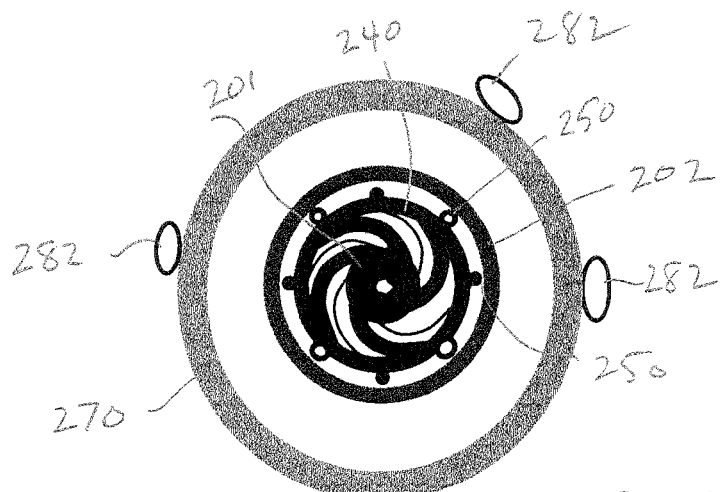
FIG. 3A is a cross-section across line 3A-3A in FIG. 3.

Referring to FIGS. 3 and 3A, when the outer catheter or sleeve 202 extends over the ablation valve 240, the multiple filaments 250 are forced into a cylindrical shape with a small cross-section suitable in size for advanced to the target location within the vessel.

Figure 4:
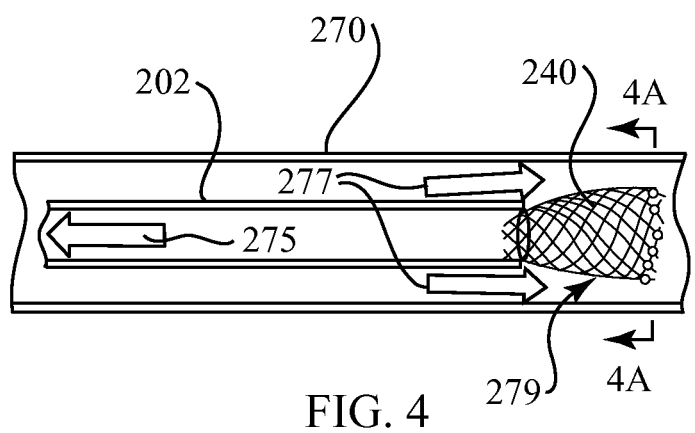
FIG. 4 is a schematic illustration of a distal end portion of the neuromodulation system of FIG. 1 in the renal artery, shown with the ablation valve released into the artery.
Figure 5:
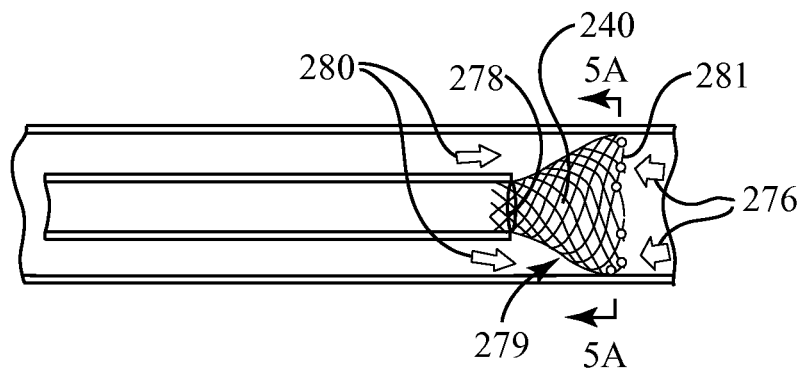
FIG. 5 is a schematic illustration of a distal end portion of the neuromodulation system of FIG. 1 in the renal artery, shown with the ablation valve expanded into contact with the endothelium of the vessel.
Figure 4A:
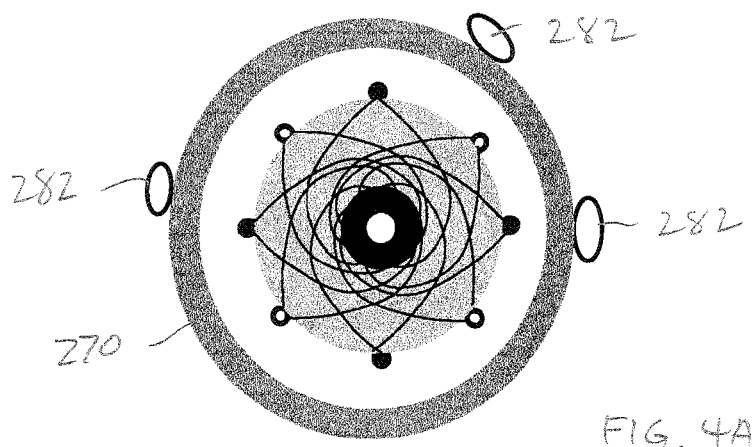
FIG. 4A is a cross-section across line 4A-4A in FIG. 4.
Figure 5A:
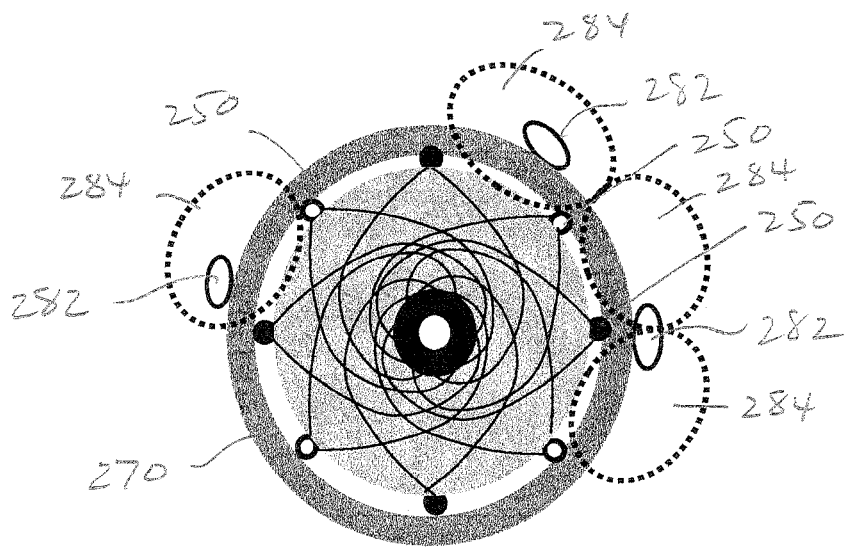
FIG. 5A is a cross-section across line 5A-5A in FIG. 5.

In the preferred embodiments, the ablation valve 240 is constrained to the introducer 201 at its proximal end where it is coupled to the distal tip 205 of the introducer 201, while the remainder of the ablation valve can either be constrained, i.e., retained within the outer sleeve 202 (FIGS. 3 and 3A), or unconstrained (FIGS. 4 through 5A). When unconstrained in the vessel 270 with retraction of the outer sleeve 202 in the direction of arrow 275 (FIG. 4), depending upon the pressure and flow conditions in the vessel and within the ablation valve 240, the ablation valve may either reach the walls of the vessel (FIGS. 5 and 5A) or it may not (FIGS. 4 and 4A). That is, the ablation valve diameter automatically changes in response to local pressure conditions about the ablation valve so as to permit forward flow of blood in the direction of arrows 277 when the pressure on the proximal surface of the ablation valve is higher than the pressure within the valve and on the distal surface of the ablation valve (FIGS. 4 and 4A). Further, the ablation valve 240 will expand to reach the endothelium 272 of the vessel 270 during brief or prolonged periods of when the pressure within and on the distal surface of the ablation valve is higher than on the proximal surface of the ablation valve, as indicated by arrows 276 (FIGS. 5 and 5A). For simplicity, the ablation valve can be considered to exist in two conditions. In a "closed" condition, the ablation valve is not uniformly in contact with the vessel inner wall 272 and blood may flow around in at least a proximal to distal direction. In an "open" condition, the ablation valve 240 expands to provide substantially uniform circumferential contact against the vessel wall 272.

At least a portion of the length of the renal artery 270 has nerves 282 extending along the exterior length thereof. Referring to FIGS. 5 and 5A, when the ablation valve 240 is in the open condition in contact with the vessel wall and the RF generator 248 powers the electrodes 264, the electrodes 264 operate to generate a pulse mode RF magnetic field 284 in at least the space occupied by the nerves 282.

Figure 6:
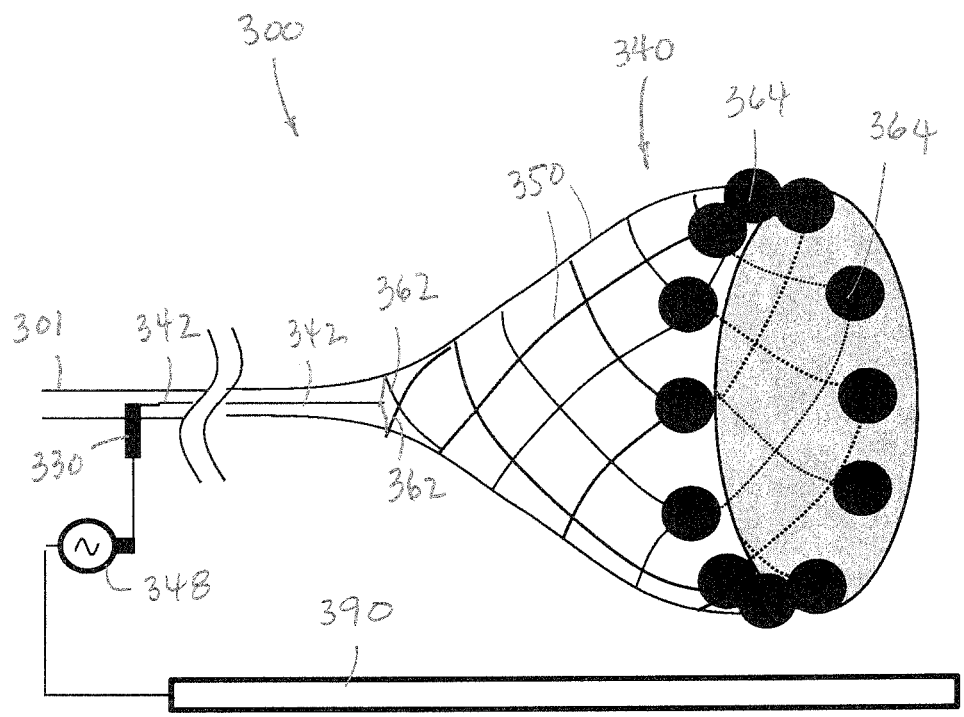
FIG. 6 is a schematic illustration of a second embodiment of a neuromodulation system according to the invention.
Figure 7:
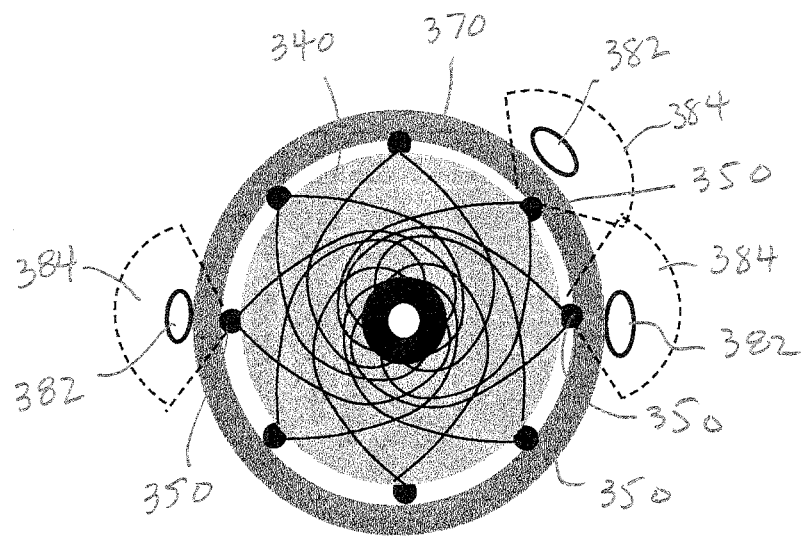
FIG. 7 is a schematic cross-section view of the ablation valve in an expanded configuration within the renal artery.

Turning now to FIG. 6, another embodiment of the device 300 is shown in the form of a monopolar device. The ablation valve 340 of the device includes filaments 350 that terminate in electrodes 364 that are not electrically isolated relative to each other. The proximal ends 362 of the filaments 350 are electrically coupled to a conductor 342 that extends along the introducer 301 to a terminal 330. The RF generator 348 is coupled to the conductor 342 at the terminal 330. A ground plate 390 is provided for placement in contact with the patient. The ablation valve dynamically operates in the same manner as described above to automatically move between open and closed conditions in contact with and out of contact with the vessel wall. As seen in FIG. 7, when the ablation valve 340 is in contact with the vessel wall and the RF generator 348 (FIG. 6) is powered, the electrodes 364 operate to generate a pulse mode RF magnetic field 384 between the electrodes 364 and the ground plate 390, with such field entering at least the space occupied by the nerves 382.

In use, a device as previously described (for purposes of description device 200 is referenced, but substantially the same method can be applied to device 300) is compressed into the lumen of a guiding catheter 202 and inserted into a femoral artery of a patient with refractory hypertension. The guiding catheter is placed a few centimeters into a renal artery 270. The guiding catheter is partially withdrawn allowing the ablation valve 240 of the device to expand such that the exposed electrodes 264 are able to contact the circumferential endothelial wall 272 of the renal artery 270. RF energy is delivered to the electrodes 264 in contact with the wall of the renal artery generating electrical conductive heating. Because of the construction of the ablation valve of the device, the ablation valve will retract from the endothelium during systole and expand and re-contact the renal artery wall during diastole. Because of the dynamic action of the ablation valve, the RF energy can be timed to the coronary cycle with energy delivered only during mid-systole. In a bipolar device, it is possible to alternate the RF energy delivery to the respective sets of interconnected wire electrodes to allow the endothelial layer of the lumen to cool. The purpose of this energy delivery is to ablate the nerve fibers adjacent to the renal artery without destroying the structural integrity of the renal artery wall. The nerve fibers will preferentially absorb energy in the same manner as purkinje fibers preferentially absorb electrical energy during ablation of the atria for atrial fibrillation. Once an area of the renal artery is treated, the entire device may be withdrawn approximately one centimeter and the RF energy delivery may be repeated. Movement and energy delivery may be repeated as needed to complete the nerve ablation process. Subsequently, the ablation valve of the device is retracted and compressed into the guiding catheter, repositioned into the contralateral renal artery, and the ablation process repeated. After ablation of the nerve fibers adjacent to both renal arteries, the ablation valve is retracted into the guiding catheter and the entire device is withdrawn from the patient.

Figure 8:
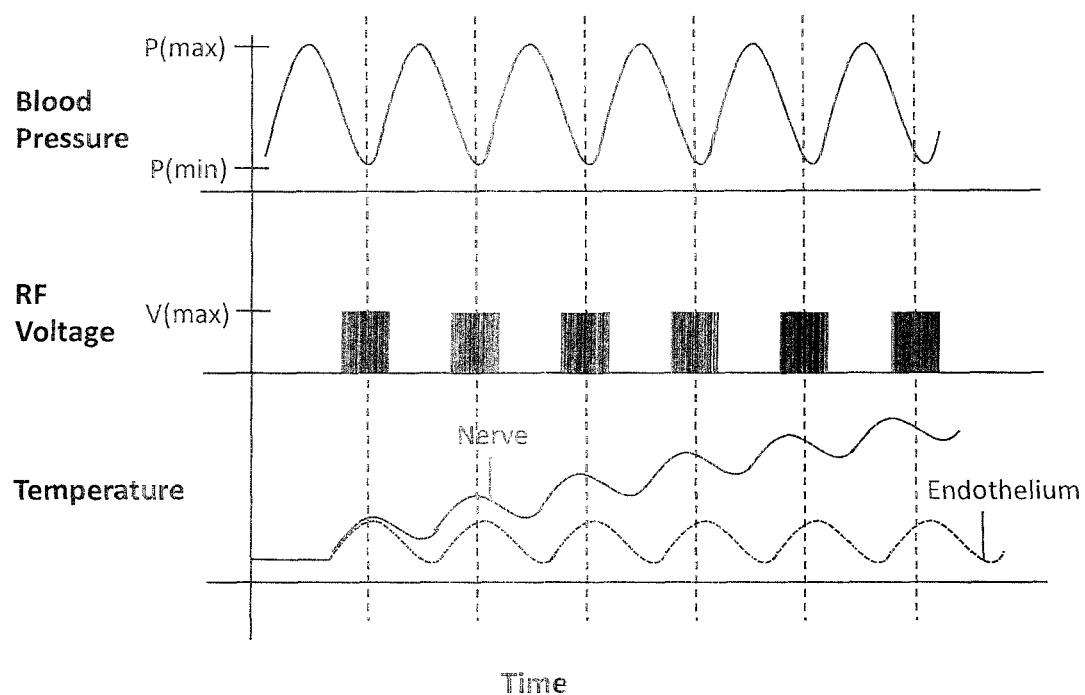
FIG. 8 illustrates the functional behavior of the device over time.
Figure 9:
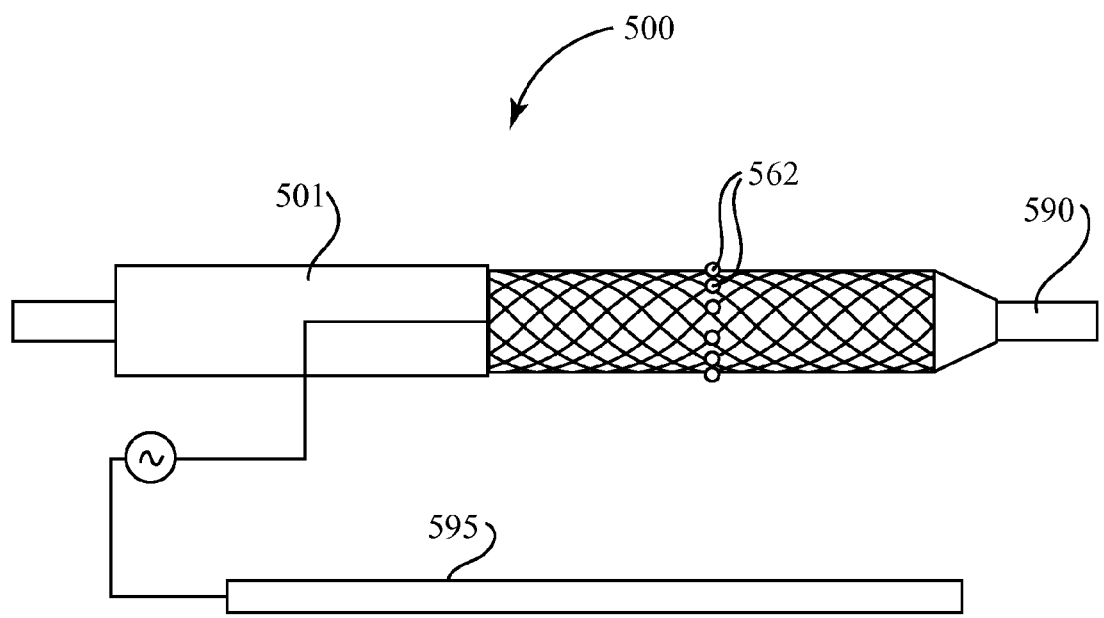
FIG. 9 is a schematic illustration of a third embodiment of a neuromodulation system according to the invention.
Figure 10:
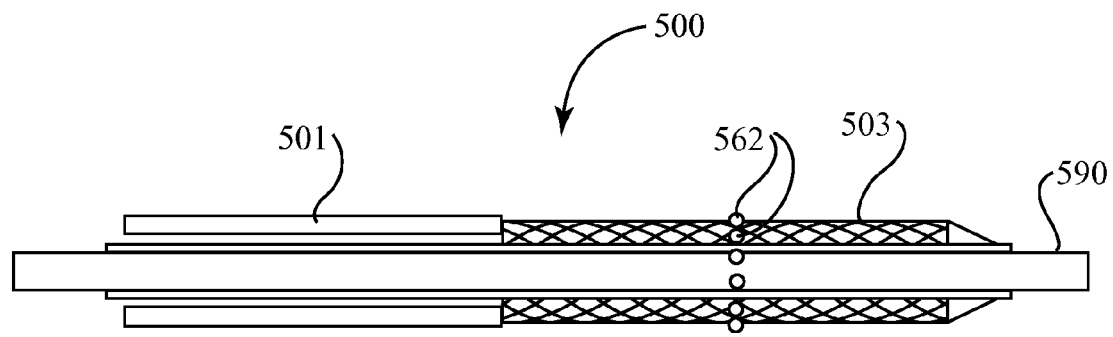
FIG. 10 is a longitudinal section view of the neuromodulation system of FIG. 9.

Referring to FIG. 8, the functional behavior of the devices in FIGS. 1 through 7 is shown. The blood pressure in the renal artery modulates the ablation valve contact with the vessel wall. The RF voltage is only applied when the device is in wall apposition. This may be gated by a physiological monitor such as a ECG 400 (FIG. 1), or detected by impedance in the RF circuit. Due to the modulation at the endothelial wall and blood flow acting as a heat transfer mechanism, the temperature in the target (nerve zone) increases to above a treatment threshold while the temperature at the non-target tissue (endothelial wall) remains below the treatment threshold.

Three parameters help define the dynamic action and performance of the ablation valve: the radial (outward) force of the ablation valve, the time constant over which the ablation valve changes condition from closed to open, and the pore size of the ablation valve.

The radial force of expansion of a braid is described by Jedwab and Clerc (*Journal of Applied Biomaterials*, Vol. 4, 77-85, 1993) and later updated by DeBeule (DeBeule et al., *Computer Methods in Biomechanics and Biomedical Engineering*, 2005) as:

$$F = 2n\left[\frac{GI_p}{K_3}\left(\frac{2\sin\beta}{K_3} - K_1\right) - \frac{EI\tan\beta}{K_3}\left(\frac{2\cos\beta}{K_3} - K_2\right)\right]$$

where $K_1$, $K_2$, $K_3$ are constants given by:

$$K_1 = \frac{\sin 2\beta_0}{D_0} \quad K_2 = \frac{2\cos^2\beta_0}{D_0} \quad K_3 = \frac{D_0}{\cos\beta_0}$$

and I and $I_p$ are the surface and polar moments of inertia of the braid filaments, E is the Young's modulus of elasticity of the filament, and G is the shear modulus of the filament. These material properties along with the initial braid angle ($\beta_0$), final braid angle ($\beta$), a tubular form (stent) diameter ($D_0$), and number of filaments (n) impact the radial force of the braided valve.

In one embodiment, the ablation valve automatically moves under force of the dynamic pressure conditions from a fully closed (undeployed) position to a fully open position in a static fluid (e.g., glycerin) having a viscosity approximately equal to the viscosity of blood (i.e., approximately 3.2 cP) in 0.067 second. For purposes herein, the time it takes to move from the fully closed position to the fully open position in a static fluid is called the "time constant". According to another aspect of the invention, the ablation valve is arranged such that the time constant of the ablation valve in a fluid having the viscosity of blood is between 0.01 seconds and 1.00 seconds. More preferably, the ablation valve is arranged such that the time constant of the valve in a fluid having the viscosity of blood is between 0.05 and 0.50 seconds. The time constant of the ablation valve may be adjusted by changing one or more of the parameters described above (e.g., the number of filaments, the modulus of elasticity of the filaments, the diameter of the filaments, etc.).

In an embodiment, the ablation valve expands fully to the vessel wall (i.e., reaches the open condition) when the pressure within and distal the ablation valve is greater than the blood pressure on the proximal surface 279 of the ablation valve, as designated by arrow 280 (FIG. 5); the ablation valve remains in a condition retreated from the vessel wall when blood is flowing downstream with a pressure on the proximal surface 279 greater than the pressure within the ablation valve (i.e., at the opening of the lumen of the catheter introducer 202) and on the distal surface of the ablation valve (FIG. 4). In addition, when the radial force of expansion of the ablation valve (i.e., the expansion force of the ablation valve itself in addition to the force of pressure within the valve and in the distal vessel over the distal surface area 281 of the valve) is greater than the radial force of compression on the ablation valve (i.e., force of pressure in the proximal vessel over the proximal surface area of the valve), the valve fully expands to the configuration shown in FIG. 5 so that the ablation valve assumes the open configuration. Thus, as seen, according to one aspect of the invention, the radial force of expansion of the ablation valve is chosen to be low (as described in more detail below) so that normal blood flow in the downstream distal direction will prevent the valve from reaching the open condition. This low expansion force is different than the expansion forces of prior art stents, stent grafts, distal protection filters and other vascular devices, which have significantly higher radial forces of expansion.

Referring back to FIGS. 1 and 2, in one embodiment, the ablation valve is constructed of an insulating fiber layer 252 formed on an 8 mm mandrel, and a braid layer 254 composed of twenty-four metal conductor filaments 250*a*, 250*b*, 250*c* . . . , each having a diameter of 0.1 mm and a final braid angle of 130° (i.e., the filaments are spring-biased or have a shape memory to assume an angle of 130° relative to each other when the valve assumes a fully deployed state and opens in a frustoconical configuration), is provided thereover. The filaments preferably have a Young's modulus greater than 200 MPa, and the ablation valve preferably has a radial force of less than 20 mN in the fully deployed position (i.e., where the filaments assume their shape memory). More preferably, the ablation valve has a radial force in the fully deployed position of less than 10 mN, and even more preferably the ablation valve has a radial force of approximately 5 mN (where the term "approximately" as used herein is defined to mean (20%) in the deployed position. This compares to prior art self-expanding embolic capture devices such as the ANGIOGUARD® (a trademark of Cordis Corporation), and prior art Nitinol stents and stent-grafts which typically have radial forces of between 40 mN and 100 mN in their fully deployed positions; i.e., radial forces generally 8 to 20 times as great.

As will be appreciated by those skilled in the art, the braid geometry and material properties are intimately related to the radial force and time constant of the valve. Since, according to one aspect of the invention, the valve is useful in a variety of arteries of different diameters and flow conditions, each implementation can have a unique optimization. By way of example only, in one embodiment, the valve has ten filaments, whereas in another embodiment, the valve has forty filaments. Preferably, the filament diameter is chosen in the range of 0.025 mm to 0.127 mm, although other diameters may be utilized. Preferably, the pitch angle (i.e., the crossing angle assumed by the filaments in the fully open position—the shape memory position) is chosen in the range of 100° to 150°, although other pitch or braid angles may be used. Preferably, the Young's modulus of the filament is at least 100 MPa, and more preferably at least 200 MPa.

According to one aspect of the invention, the fiber layer has a characteristic pore size between 10 μm and 500 μm. More preferably, the fiber layer has a characteristic pore size between 15 μm and 100 μm. Even more preferably, the fiber layer has a characteristic pore size of less than 40 μm and more preferably between 20 μm and 40 μm. Most desirably, the fiber layer is provided with a characteristic pore size that will permit highly pressurized blood to pass therethrough. By allowing blood to flow back through the fiber layer, even at a relatively slow rate, backpressure on the distal side of the valve can be alleviated.

The fiber layer 252 is also preferably provided with a hydrophilic coating, hydrophobic coating, or other coating that affects how proteins within blood adhere to the fiber layer and specifically within the pores of the fiber layer. More specifically, the coating is resistant to adhesion of blood proteins. One coating that has been used successfully is ANTI-FOG COATING 7-TS-13 available from Hydromer, Inc. of Branchburg, N.J., which can be applied to the filter by, e.g., dipping, spraying, roll or flow coating.

By appropriate design of the pore size and use of an appropriate coating, proteins in the blood will almost immediately fill the pores during use. The proteins on the coated porous fiber layer operate as a pressure safety valve, such that the pores are filled with the proteins when subject to an initial fluid pressure greater than the blood vessel pressure, but the proteins are displaced from the pores and the pores are opened to blood flow at higher pressures such as a designated threshold pressure. The designated threshold pressure is determined to prevent damage to the tissue and organs, and injury to the patient. Thus, this system allows a pressure greater than the vessel pressure while limiting very high pressures which may be unsafe to the patient. As such, the system provides pressure regulation which is not possible with other occlusive devices, including balloons. Notwithstanding the advantage of the above, it is not a requirement of the invention that the fiber layer be constructed to allow blood to pass through in the upstream 'reflux' direction under any determined pressure.

As described above, the radial force of expansion on the ablation valve is chosen such that normal blood flow in the downstream distal direction in systole will prevent the valve from reaching the open condition. However, the radial force of expansion is such that normal blood flow in the downstream distal direction during diastole allows the valve to reach the open condition and make circumferential contact with the vessel wall.

In a preferred embodiment of the invention, the introducer is a catheter and the surgeon can actively alter the fluid pressure relative to the ablation valve to modify the state of the ablation valve, regardless of the force of the blood pressure on the proximal and distal surfaces of the ablation valve, via the injection of a fluid, such as saline, through the lumen of the introducer. Such fluid is preferably also a thermal fluid which operates to further remove and dissipate heat within the vessel from the operation of the system. With the introducer as a catheter, the surgeon can simultaneously, or substantially simultaneously, (i) move the ablation electrodes from a disengaged position (out of contact with vessel wall) to an engaged position (in contact with the vessel wall) and (ii) provide thermal cooling through the catheter to the ablation site to prevent tissue damage to non-target tissue. Upon such infusion the pressure changes at the distal opening of the lumen. When the pressure at the distal opening of the introducer (inside the expandable ablation valve) increases higher than the pressure in the blood vessel, the expandable ablation valve substantially immediately opens and seals the exposed ablation electrodes to the blood vessel wall. It is important to note that pressure is communicated within the introducer and throughout the vasculature at the speed of sound in blood (1540 m/s) and that the ablation valve opens and closes in response to pressure changes within the blood vessel. Since the ablation valve responds to pressure changes, it reacts extremely fast. Simultaneously (or proximate with) with the infusion of the fluid and expansion of the ablation valve, the RF generator is gated to energize the electrodes to neuromodulate the renal nerve for effective renal denervation. Given the rapid action of the ablation valve in response to the pressure changes, the RF generator can be gated to activate upon and immediately thereafter the infusion of the thermal fluid through the introducer. This ensures that the RF energy is applied to the ablation electrodes only when the ablation electrodes are in contact with the vessel wall. Moreover, when the pressure through the introducer is reduced to provide lower pressure on a distal side of the ablation valve than the proximal side thereof, the valve closes permitting blood to flow through the vessel. This further allows removal of remaining heat from the treatment site. Further, blood flow is only momentarily stopped by the ablation valve during relatively high pressure infusion of the thermal fluid and active ablation.

Figure 11:
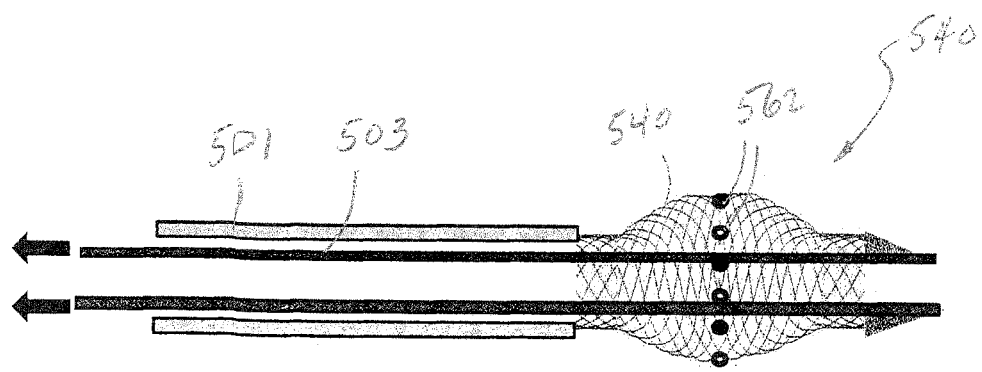
FIG. 11 illustrates operation of the neuromodulation system of FIG. 9.
Figure 12:
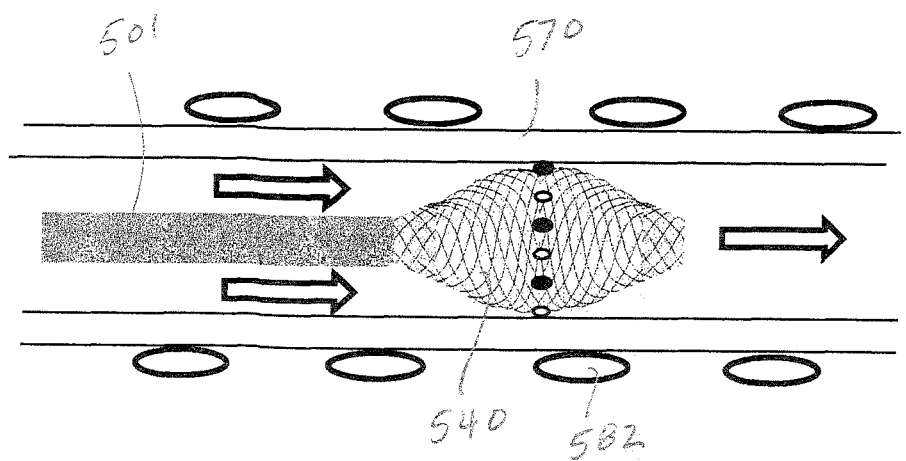
FIG. 12 shows operation of the neuromodulation system of FIG. 9 within the artery.
Figure 13:
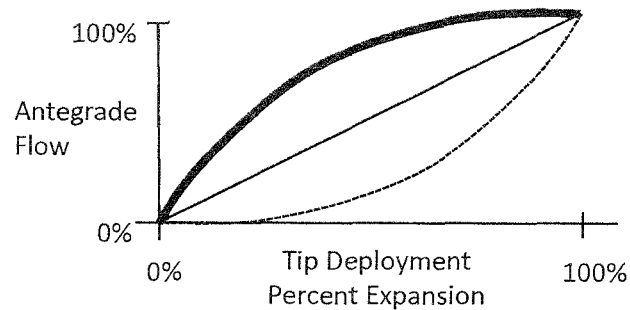
FIG. 13 is a graph of three different curves relating antegrade flow relative to the expansion of the ablation valve (tip).
Figure 14:
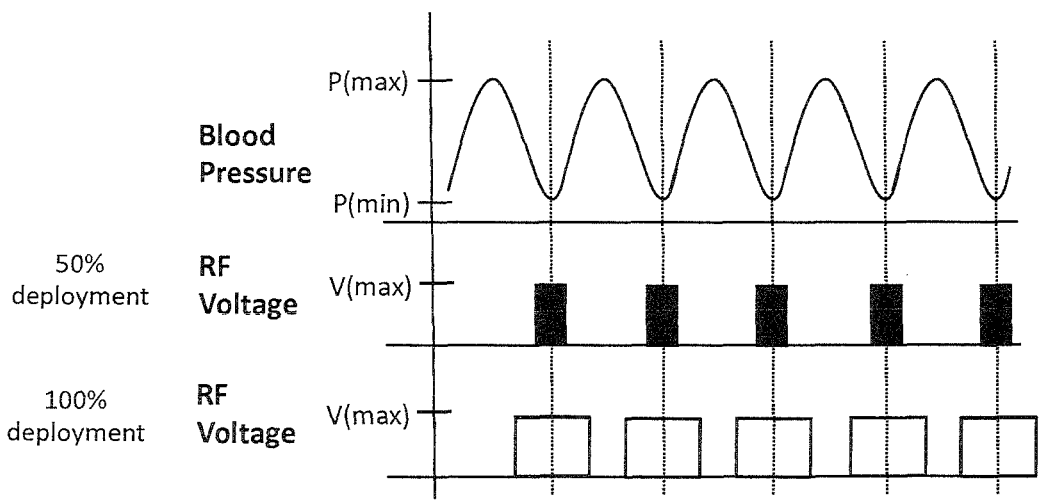
FIG. 14 is a duty cycle timing chart for the third embodiment.
Figure 15:
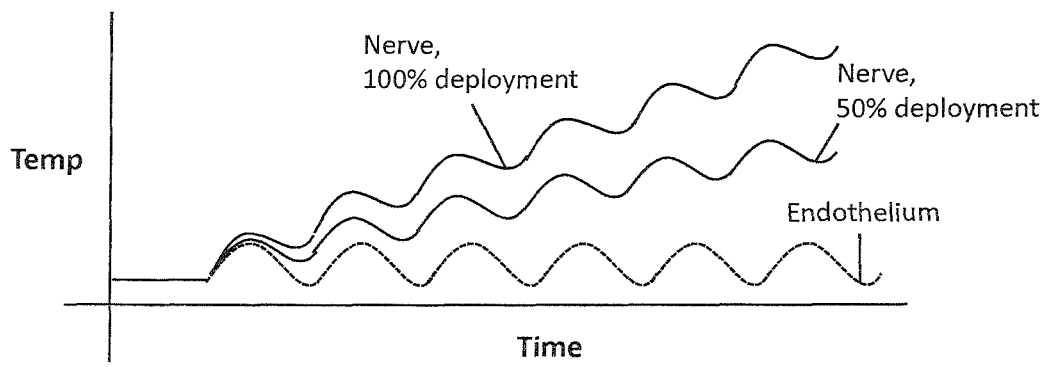
FIG. 15 illustrates the impact of the duty cycle on the time to treatment threshold.

Turning now to FIGS. 9 through 12, another embodiment of a device 500 for neuromodulation of a renal nerve about a renal artery is shown. The device 500 includes two concentric catheter bodies 501, 503. The outer catheter body 501 is fused to the proximal end of an expandable ablation valve 540, and the inner catheter body 503 is fused to a distal end of the expandable ablation valve 540. Exposed electrodes 562 from the braid comprising the ablation valve are provided at the center of the ablation valve. Movement of the inner body 503 relative to the outer body 501 changes the diameter of the ablation valve and radially displaces the electrodes. More particularly, when the inner catheter body 503 is advanced relative to the outer catheter body 501, the ablation valve 540 radially collapses into the configuration shown FIGS. 9-10, such that it is dimensionally suitable for advancement through the femoral artery, aorta, and into the renal artery. In such configuration, the device can be advanced over a guidewire 590 to the treatment site. Once at the treatment site, the guidewire 590 is removed. Then, as the inner catheter body 503 is retracted, the ablation valve 540 expands (FIGS. 11 and 12). Decreasing the distance between the distal ends of the inner and outer catheters 501, 503 expands the ablation valve such that the ablation valve 540 exerts greater outward force and subsequently can be used to increase the neuromodulation energy at the treatment site and affect the duty cycle of the ablation valve. Referring to FIG. 13, a graph of three different curves relating downstream flow past the ablation valve to the percentage expansion of the ablation valve. Mechanical properties of the expandable tip such as coating thickness, filament thickness, number of filaments in the braid, and the amount of bonding in the coating can create either an under driven system (dotted line), a linear system (solid line), or an over driven system (thick line). The over driven system very quickly occludes flow and creates a much higher duty cycle for treatment. In addition, manually exerted force between the inner and outer catheters 501, 503 can effect a modification in duty cycle. That is, referring to FIG. 14, if the inner and outer catheters 501, 503 are manipulated to only partially expand the ablation valve 540 (e.g., 50% relative to a maximum diameter) but with the electrodes nevertheless in contact with the endothelium, the duty cycle of the device is lower. Likewise, if the inner and outer catheters 501, 503 are manipulated to substantially greater expand the ablation valve 540 (e.g., approaching 100% relative to a maximum diameter), the duty cycle of the device is higher. Referring to FIG. 15, with a lower duty cycle, the temperatures generated at the treatment site are kept lower, but a longer time may be required to reach satisfactory treatment. With a higher duty cycle, it will be faster to reach treatment threshold, but higher temperatures may be generated at the endothelium.

The device 500 may be configured as either a bipolar or monopolar system. In a monopolar system, a grounding plate 595 is coupled to the RF generator 548, as described above (FIG. 9). The RF generator may be gated for application of energy using any suitable system, including any of the means described above.

In any of the embodiments described herein, the components of the valve may be coated to reduce friction in deployment and retraction. The components may also be coated to reduce thrombus formation along the valve or to be compatible with therapeutics, biologics, or embolics. The components may be coated to increase binding of embolization agents so that they are removed from the vessel during refraction.

According to one aspect of the invention, the catheter body and ablation valve may be separately labeled for easy visualization under fluoroscopy. The catheter body can be labeled by use of any means known in the art; for example, compounding a radio-opaque material into the catheter tubing. The radio-opaque material can be barium sulfate, bismuth subcarbonate or other material. Alternatively or additionally, radio-opaque rings can be placed or crimped onto the catheter, where the rings are made of platinum, platinum iridium, gold, tantalum, and the like. The ablation valve may be labeled by crimping a small radio-opaque element such as a ring on one or a plurality of filaments. Alternatively or additionally, radio-opaque medium can be compounded into the materials of the braid and the fiber layer. Or, as previously described, one or more of the filaments may be chosen to be made of a radio-opaque material such as platinum iridium.

There have been described and illustrated herein embodiments of devices and methods for neuromodulation of a nerve about a vessel. While particular embodiments of the invention have been described, it is not intended that the invention be limited thereto, as it is intended that the invention be as broad in scope as the art will allow and that the specification be read likewise. Thus, while the invention has been described with respect to particular vessels of humans, it will be appreciated that the invention can have application to any blood vessel and other vessels, including ducts, of humans and animals. Further, the embodiments have been described with respect to their distal ends because their proximal ends can take any of various forms, including forms well known in the art. By way of example only, the proximal end can include two handles with one handle connected to the inner (delivery) catheter, and another handle connected to an outer catheter or sleeve or actuation wire or string. Movement of one handle in a first direction relative to the other handle can be used to deploy the ablation valve, and where applicable, movement of that handle in an opposite second direction can be used to withdrawn the ablation valve into the delivery catheter. Depending upon the handle arrangement, valve deployment can occur when the handles are moved away from each other or towards each other. As is well known, the handles can be arranged to provide for linear movement relative to each other or rotational movement. If desired, the proximal end of the inner catheter can be provided with hash-marks or other indications at intervals along the catheter so that movement of the handles relative to each other can be visually calibrated and give an indication of the extent to which the valve is opened. It will therefore be appreciated by those skilled in the art that yet other modifications could be made to the provided invention without deviating from its scope as claimed.

We claim:

1. A neuromodulation device for use in a vessel having an endothelium and carrying body fluid with a fluid pressure, comprising:
   a) an elongate flexible introducer having a proximal end and distal end;
   b) an expandable ablation valve at said distal end of said introducer, said ablation valve having a proximal surface, a distal surface, a circumference, and a plurality of electrodes displaced about said circumference, said ablation valve adapted to dynamically react to fluid pressure within the vessel such that,
      i) when a pressure within and on said distal surface of said ablation valve is less than the fluid pressure on said proximal surface of said ablation valve, said ablation valve is in a retreated configuration in which said electrodes are configured to be out of circumferential contact with the endothelium of the vessel, and
      ii) when said pressure within and on said distal surface of said ablation valve is greater than the fluid pressure on said proximal surface of said ablation valve, said ablation valve is in a contact configuration in which said electrodes are configured to be in circumferential contact with the endothelium of the vessel; and
   c) a conductor extending along said introducer, said conductor having a distal end electrically coupled to said electrodes of said ablation valve and a proximal end extended to a terminal for coupling to a RF generator.

2. A neuromodulation device according to claim 1, wherein:
   said introducer is a catheter defining a lumen having a distal opening that is located at an interior of said ablation valve.

3. A neuromodulation device according to claim 1, wherein:
   a proximal end of said ablation valve is located substantially coincident with said distal opening of said lumen.

4. A neuromodulation device according to claim 1, wherein:
   said ablation valve expands to said contact configuration during diastole, and moves to said retreated configuration during systole.

5. A neuromodulation device according to claim 1, wherein:
   said ablation valve comprises an inner layer defined by electrospun fibers, and an expandable structure over said inner layer comprising a braid of filaments which cross over each other, at least a plurality of said filaments having a spring bias to assume a preferred crossing angle relative to each other, a proximal end of said braid of filaments radially collapsed and coupled to the distal end of said elongate introducer.

6. A neuromodulation device according to claim 5, wherein:
   in each of said contact configuration and said retreated configuration, said ablation valve has respective frusto-conical shapes.

7. A neuromodulation device according to claim 5, wherein:
   said filaments define at least a plurality of electrodes.

8. A neuromodulation device according to claim 7, wherein:
   said filaments comprise insulated wires, and each said electrode is defined at a portion of said wire at which a portion of the insulation has been removed to expose an interior conductive metal of said wire.

9. A neuromodulation device according to claim 7, wherein:
   said filaments include non-conductive filaments.

10. A neuromodulation device according to claim 7, wherein:
    an outer layer of electrospun fibers provided over said filaments.

11. A neuromodulation device according to claim 7, wherein:
    said device is bipolar.

12. A neuromodulation device according to claim 11, wherein:
    said electrodes includes first and second electrically isolated sets of electrodes, and said conductor comprises first and two electrically isolated conductors, said first conductor electrically coupled to said first set of electrodes, and said second electrode coupled to said second set of electrodes.

13. A neuromodulation device according to claim 7, wherein:
    said device is monopolar.

14. A neuromodulation device according to claim 1, further comprising:
    a sleeve into which said introducer and ablation valve are provided for delivery to a treatment site, said introducer longitudinally displaceable relative to said sleeve to advance said ablation valve out of a distal end of said sleeve.

15. A neuromodulation device according to claim 1, further comprising:
    an inner catheter having a proximal end and a distal end and extending through said introducer, wherein a distal end of said ablation valve is coupled to said distal end of said inner catheter, and said inner catheter and introducer are longitudinally translatable relative to each other to move said ablation valve between said open and closed configurations.

16. A neuromodulation device according to claim 1, further comprising:
    said RF generator electrically coupled to said terminal.

17. A neuromodulation device for use in a vessel having an endothelium and carrying body fluid with a fluid pressure, comprising:

a) an elongate flexible introducer having a proximal end and distal end;
b) an expandable ablation valve at said distal end of said introducer, said ablation valve having a first surface, an opposing second surface, a circumference, and a plurality of electrodes displaced about said circumference, said ablation valve adapted to dynamically react to fluid pressure within the vessel such that,
   i) when a pressure within and on said second surface of said ablation valve is less than the fluid pressure on said first surface of said ablation valve, said ablation valve is in a retreated configuration in which said electrodes are configured to be out of circumferential contact with the endothelium of the vessel, and
   ii) when said pressure within and on said second surface of said ablation valve is greater than the fluid pressure on said first surface of said ablation valve, said ablation valve is in a contact configuration in which said electrodes are configured to be in circumferential contact with the endothelium of the vessel; and
c) a conductor extending along said introducer, said conductor having a distal end electrically coupled to said electrodes of said ablation valve and a proximal end extended to a terminal for coupling to a RF generator.

* * * * *